United States Patent
Stephenson et al.

(10) Patent No.: US 8,905,030 B2
(45) Date of Patent: Dec. 9, 2014

(54) TRACHEAL TUBE WITH CONNECTOR INSERT

(75) Inventors: James Stephenson, Galway (IE); Paul Waldron, Galway (IE)

(73) Assignee: Covidien LP, Mansfield, MA (US)

( * ) Notice: Subject to any disclaimer, the term of this patent is extended or adjusted under 35 U.S.C. 154(b) by 343 days.

(21) Appl. No.: 13/076,729

(22) Filed: Mar. 31, 2011

(65) Prior Publication Data

US 2012/0247477 A1  Oct. 4, 2012

(51) Int. Cl.
*A61M 16/04* (2006.01)
*A61M 16/08* (2006.01)

(52) U.S. Cl.
CPC .......... *A61M 16/04* (2013.01); *A61M 16/0816* (2013.01); *A61M 16/0434* (2013.01); *A61M 16/0497* (2013.01); *A61M 16/0465* (2013.01); *A61M 16/0479* (2014.02)
USPC ........... 128/207.14; 128/200.24; 128/200.26; 128/202.27

(58) Field of Classification Search
CPC .......... A61M 16/04; A61M 16/0475; A61M 16/0479; A61M 16/0486; A61M 16/0816; A61M 16/0465
USPC ............. 128/207.14, 202.27, 200.26, 207.15, 128/200.24
See application file for complete search history.

(56) References Cited

U.S. PATENT DOCUMENTS

| | | | |
|---|---|---|---|
| 3,964,488 A | | 6/1976 | Ring et al. |
| 3,973,569 A | * | 8/1976 | Sheridan et al. ......... 128/207.15 |
| 4,033,353 A | * | 7/1977 | La Rosa .................... 128/207.15 |
| 4,052,990 A | * | 10/1977 | Dodgson .................. 128/207.14 |
| 4,146,034 A | | 3/1979 | Gupta |
| 4,152,017 A | | 5/1979 | Abramson |
| 4,166,468 A | * | 9/1979 | Haynie ..................... 128/207.15 |
| 4,369,991 A | | 1/1983 | Linder |
| 4,475,548 A | | 10/1984 | Muto |
| 4,683,879 A | | 8/1987 | Williams |
| 4,909,248 A | | 3/1990 | McLennan Anderson |
| 5,251,617 A | | 10/1993 | Linder |

(Continued)

FOREIGN PATENT DOCUMENTS

| | | |
|---|---|---|
| EP | 2086619 | 8/2009 |
| FR | 2725627 | 4/1996 |

(Continued)

OTHER PUBLICATIONS http://oxforddictionaries.com/us/definition/american_english/recess (c) Oxford University Press.*

(Continued)

*Primary Examiner* — Annette Dixon
(74) *Attorney, Agent, or Firm* — Fletcher Yoder PC

(57) ABSTRACT

A tracheal tube assembly includes a connector body, a cannula extending from the connector body, and an insert that provides rigidity to the connector body and retains the cannula in the connector body. The cannula has an upper end that fits between conforming tapered sections of the connector body inner surface and the insert. The insert may include features to mitigate stress on and around any secondary lumens in the cannula wall. Because the wall is thinner at the site of a secondary lumen, the connector body insert may include a recess into which the cannula wall may expand. The recess may be aligned with the secondary lumen.

20 Claims, 5 Drawing Sheets

(56) References Cited

U.S. PATENT DOCUMENTS

| | | | |
|---|---|---|---|
| 5,259,376 A | | 11/1993 | Bales |
| 5,279,610 A | * | 1/1994 | Park et al. .................. 606/108 |
| 5,333,608 A | | 8/1994 | Cummins |
| 5,460,176 A | * | 10/1995 | Frigger .................. 128/207.14 |
| 5,464,011 A | | 11/1995 | Bridge |
| 5,487,731 A | | 1/1996 | Denton |
| 5,579,762 A | * | 12/1996 | Lee .................. 128/207.14 |
| 5,590,647 A | | 1/1997 | Nye |
| 5,740,796 A | | 4/1998 | Skog |
| 5,794,986 A | * | 8/1998 | Gansel et al. ............ 285/148.16 |
| 5,864,938 A | * | 2/1999 | Gansel et al. .................. 29/506 |
| 5,865,176 A | * | 2/1999 | O'Neil .................. 128/207.15 |
| 5,906,204 A | | 5/1999 | Beran et al. |
| 6,102,041 A | | 8/2000 | Boussignac et al. |
| 6,248,099 B1 | * | 6/2001 | Bell .................. 604/533 |
| 6,722,369 B1 | | 4/2004 | Kron |
| 6,802,316 B1 | | 10/2004 | Fulgham |
| 6,994,088 B2 | | 2/2006 | Briggs |
| 7,086,402 B2 | | 8/2006 | Peterson |
| 7,156,827 B2 | | 1/2007 | McNary et al. |
| 7,293,561 B2 | | 11/2007 | Madsen et al. |
| 7,448,387 B2 | | 11/2008 | Janatpour |
| 7,600,515 B2 | | 10/2009 | Matlock |
| 7,654,264 B2 | | 2/2010 | Clayton |
| 7,681,576 B2 | * | 3/2010 | Thomas et al. .......... 128/207.29 |
| 8,316,845 B2 | * | 11/2012 | Tappehorn et al. ...... 128/202.27 |
| 2003/0037789 A1 | * | 2/2003 | Klinberg et al. ......... 128/207.14 |
| 2003/0196659 A1 | | 10/2003 | Gradon et al. |
| 2004/0238776 A1 | | 12/2004 | Peters et al. |
| 2005/0161047 A1 | | 7/2005 | Briggs |
| 2005/0166924 A1 | | 8/2005 | Thomas et al. |
| 2006/0184137 A1 | | 8/2006 | Reynolds |
| 2006/0235357 A1 | | 10/2006 | Woodward et al. |
| 2007/0044806 A1 | | 3/2007 | Madsen et al. |
| 2007/0083262 A1 | | 4/2007 | Matlock |
| 2007/0255258 A1 | | 11/2007 | Matlock et al. |
| 2008/0009798 A1 | | 1/2008 | Bianco |
| 2008/0041391 A1 | * | 2/2008 | Worley .................. 128/207.14 |
| 2008/0072911 A1 | | 3/2008 | Flagler et al. |
| 2008/0149108 A1 | | 6/2008 | Neame |
| 2008/0216839 A1 | | 9/2008 | Rutter |
| 2010/0037898 A1 | | 2/2010 | Matlock |
| 2010/0154800 A1 | * | 6/2010 | Chang et al. ............ 128/207.15 |
| 2010/0307488 A1 | | 12/2010 | Poulsen et al. |
| 2010/0319705 A1 | | 12/2010 | Thomas et al. |
| 2011/0197895 A1 | * | 8/2011 | Stephenson et al. ..... 128/207.14 |
| 2011/0290254 A1 | | 12/2011 | Waldron |
| 2012/0103341 A1 | | 5/2012 | Behlmaier |

FOREIGN PATENT DOCUMENTS

| | | |
|---|---|---|
| GB | 2309907 | 8/1997 |
| WO | WO9824500 | 6/1998 |
| WO | WO2009/087347 | 7/2009 |
| WO | WO2008046418 | 8/2009 |

OTHER PUBLICATIONS

PCT/US2011/036030 International Search Report & Written Opinion mailed Aug. 19, 2011.

Makino, Hiroshi MD et al., The Effects of Tracheal Tube Tip Design and Tube Thickness on Laryngeal Pass Ability During Oral Tube Exchanger with an Introducer, Anesthesia and Analgesia, Dec. 2003, pp. 285-288, Issue 97.

Lee, Chao-Hsien et al., Dexamethasone to Prevent Postextubation Airway Obstruction in Adults: A Prospective, Randomized, Double-Blind, Placeo-Controlled Study, Critical Care, Jul. 2007, p. R72, Article 11.

Flex-C-PAP, Teleflex Medical—Hudson RCI, Apr. 2010, pp. 1-2.

Rusch Disposable Inner Cannula, http://www.teleflexmedical.com/prod_rusch.php, 2010, pp. 1-5.

Rusch, Easytube Double Lumen, Teleflex Medical, http://www.teleflexmedical.com/prod_rusch.php, 2009, pp. 1-7.

Sheridan Performed Endotracheal Tubes, Teleflex Medical—Hudson RCI, Apr. 2010, pp. 1-3.

Sheridan LITA Cuffed Endotracheal Tube and STAT-Med Cuffed Endotracheal Tube, Teleflex Medical—Hudson RCI, Apr. 2010, pp. 1-3.

Silicone Cuffless and Silicon Cuffless Extended Connect Pediatric & Neonatal Tracheostomy Tubes, Arcadia Medical, http://www.arcadiamedical.com/arcadia/main.asp?cid=4&pid=4, 2010, pp. 1-2.

Tracoe Medical GmbH-Percutan, http://tracoe.com/products.html. 2010, pp. 1-4.

Tracoe Medical GmbH-twist, http://tracoe.com/products/4/twist.html. 2010, pp. 1-4.

U.S. Appl. No. 12/788,569, filed May 27, 2010, Waldron et al.

U.S. Appl. No. 12/916,297, filed Oct. 29, 2010, Behlmaier.

* cited by examiner

TRACHEAL TUBE WITH CONNECTOR INSERT

BACKGROUND

The present disclosure relates to a tracheal tube, and more particularly to a tracheal tube having a connector insert for securing a cannula to the connector.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide range of applications exist for artificial ventilation that may call for the use of tubes that are inserted into a patient. Such tubes may include endotracheal tubes, tracheostomy tubes, and so forth. In the former case, the tubes are typically inserted through the mouth and into the trachea. In the latter, the tubes are often inserted into an opening formed in the neck and trachea of the patient. In both cases, the tubes may be used for artificial ventilation or for assisting patient ventilation. They are typically designed to interface with standard connectors that are located at the end of a ventilation hose assembly which itself may be connected to a ventilator.

Current designs for such tubes may allow for easy connection to an upper connector, but may have various structures, some quite complex, for conveying air between the connector and a cannula that extends into the patient. In some cases, a soft plastic or rubber is used for the connector, providing a seal with the interfacing ventilation assembly. Moreover, difficulties exist in the mounting of the cannula in such devices, which must interface with the connector portion to provide the desired airflow path. The sizes of such cannulas may vary substantially, depending upon the anatomy of the patient, the age of a patient, and so forth. For example, the inner diameter of cannulas for pediatric and neonatal patients may vary between 2.5 mm and 6.5 mm. Larger sizes may be provided, but it would be desirable to have a uniform system of attachment between the cannula and the connector independent of the size. In addition, because the interface between the cannula and the connector involves a compression fit, the relatively softer cannula may break or split under certain types of stresses.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
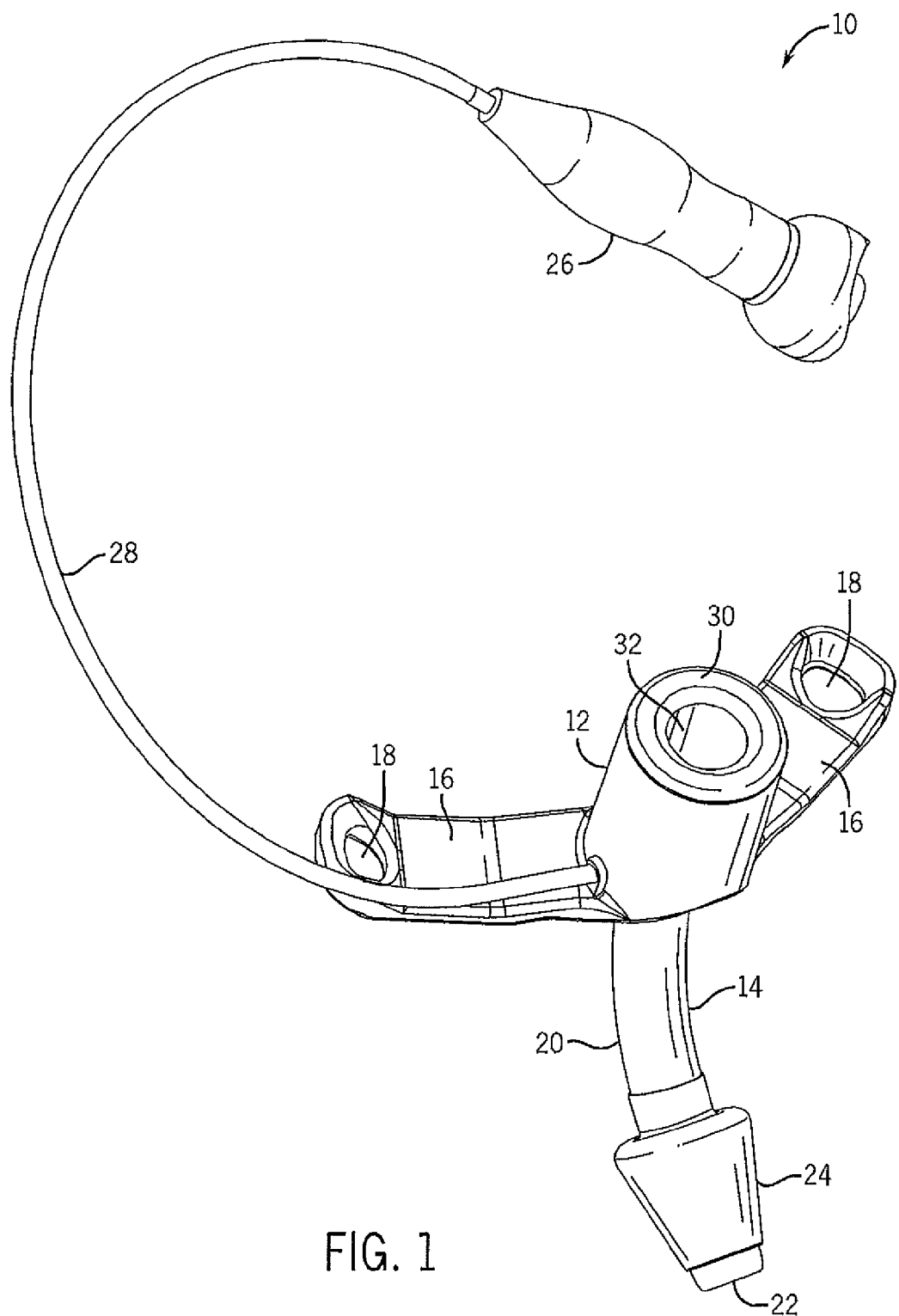
FIG. 1 is a perspective view of a tracheal tube in accordance with aspects of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Tracheal tubes are connected to a ventilation circuit via one or more connecting pieces. Typically, tracheal tubes are provided with integral connecting pieces at their proximal ends to facilitate connection to the appropriate upstream tubing and respiratory gas source. In particular embodiments, the connecting pieces may include an assembly for directing a cuff inflation line, allowing limited movement of the connector and respiratory circuit tubing relative to the tracheal tube.

Tracheal tubes and similar devices are disclosed in the present discussion that have connecting pieces with recessed or notched portions to accommodate certain features at the proximal end of a tracheal tube. For example, tracheal tubes may include one or more secondary lumens formed in or on the wall of the tube. The wall of the tracheal tube is thinner at the location of any secondary lumens. Accordingly, when the tracheal tube is compressed or stretched around a connector at the proximal end, the tube wall may split open around the secondary lumen. Because the connectors are typically inserted into the tube during manufacturing, any splitting of the tube may lead to a decreased manufacturing yield and connections of degraded quality. In certain embodiments, connectors with recesses or notches sized and shaped to accommodate the secondary lumens reduce the stress applied to the tube wall at its weakest locations. For example, the compression forces on the wall are reduced because the tube may expand into a recess on the connector. One or more recessed or notched areas of the connector are aligned with the location of any secondary lumens to prevent splitting of the tube. Such recesses may also be designed to avoid or reduce closure of the secondary lumens that may occur from hoop and/or compressive stresses applied by the connecting components.

In certain embodiments, the present techniques may be used in conjunction with any appropriate medical device, including a feeding tube, an endotracheal tube, a tracheostomy tube, a bronchocatheter, a circuit, an airway accessory, a connector, an adapter, a filter, a humidifier, a nebulizer, nasal cannula, or a laryngeal mask. The present techniques may also be used to monitor any patient benefiting from mechanical ventilation. Further, the devices and techniques provided herein may be used in conjunction with any appropriate medical connector or medical tubing.

FIG. 1 illustrates an exemplary tracheal tube in accordance with the present disclosure, designated generally by reference numeral 10. In the illustrated embodiments, the tracheal tube is designed as a tracheostomy tube, although the present assembly techniques could be used in other tubes, such as endotracheal tubes and so forth. In the illustrated embodiment, the tracheal tube 10 includes an end connector 12 designed to be attached to an artificial ventilation system. Various sized of such connectors are available, and the connector may be dimensioned to accommodate any one of these sizes. In the illustrated embodiment, the connector has an outer diameter of approximately 15 mm to conform to ISO standard dimensions of mating connectors. A cannula 14 (e.g., ventilation lumen) extends from a lower end of the connector and is designed for insertion into the airway of a patient. Moreover, side flanges 16 extend from the connector for facilitating securement of the device to a patient. In the cse of the tracheal tube shown, the flanges 16 may terminate in apertures 18 through which straps or other attachments devices can be inserted. The tracheal tube may be held in place on the neck of a patient by such straps. It should be noted that certain arrangements that incorporate the present teachings, such as endotracheal tubes, may not be provided with flanges.

In the illustrated embodiment, the cannula 14 is a hollow tube that can direct air or other ventilation gasses into and out of a patient. To conform more aptly to the patient anatomy, a curved section 20 may be provided as shown. The curved section ends in a lower or distal tip 22 which will be lodged in the patient during use. In certain embodiments, the distal tip 22 may include a beveled edge enabling a smoother insertion of the cannula 14 into the patient's trachea. The illustrated cannula 14 includes an inflatable cuff 24 designed to seal the patient's airway. The cuff 24 may be connected to a cuff inflator valve 26 through an inflation lumen 28. The cuff inflator valve 26 may deliver a gas, such as air, through the inflation lumen 28 and into the cuff 24, thus inflating the cuff 24. The cuff 24, when inflated, will expand radially around the cannula 14 and seal the patient's airway. By using one or more cuffs 24 to seal the patient's airway, substances may flow only through the cannula 14 (or other medical device), allowing better control over the type and amount of substances flowing into and out of the patient.

The end connector 12 further includes an insert 30 which is disposed inside the connector body as described more fully below. As also described below, the insert serves to rigidify the connector body and to retain the cannula within the connector body. The insert may also include a top surface. Moreover, the insert 30 may assist in preventing rotation of the cannula within the connector body. An air passageway 32 is formed through the insert 30 and extends through the cannula such that, when coupled to appropriate ventilation devices, air or other gasses may be freely exchanged between the upper or proximate end of the connector and the distal end 22 of the cannula 14. In an alternate embodiment, the features of the insert 30 and the connector 12 may be formed as a unitary assembly, e.g., a single molded piece. In such an embodiment, the insert 30 is an integral component of the connector 12.

Figure 2:
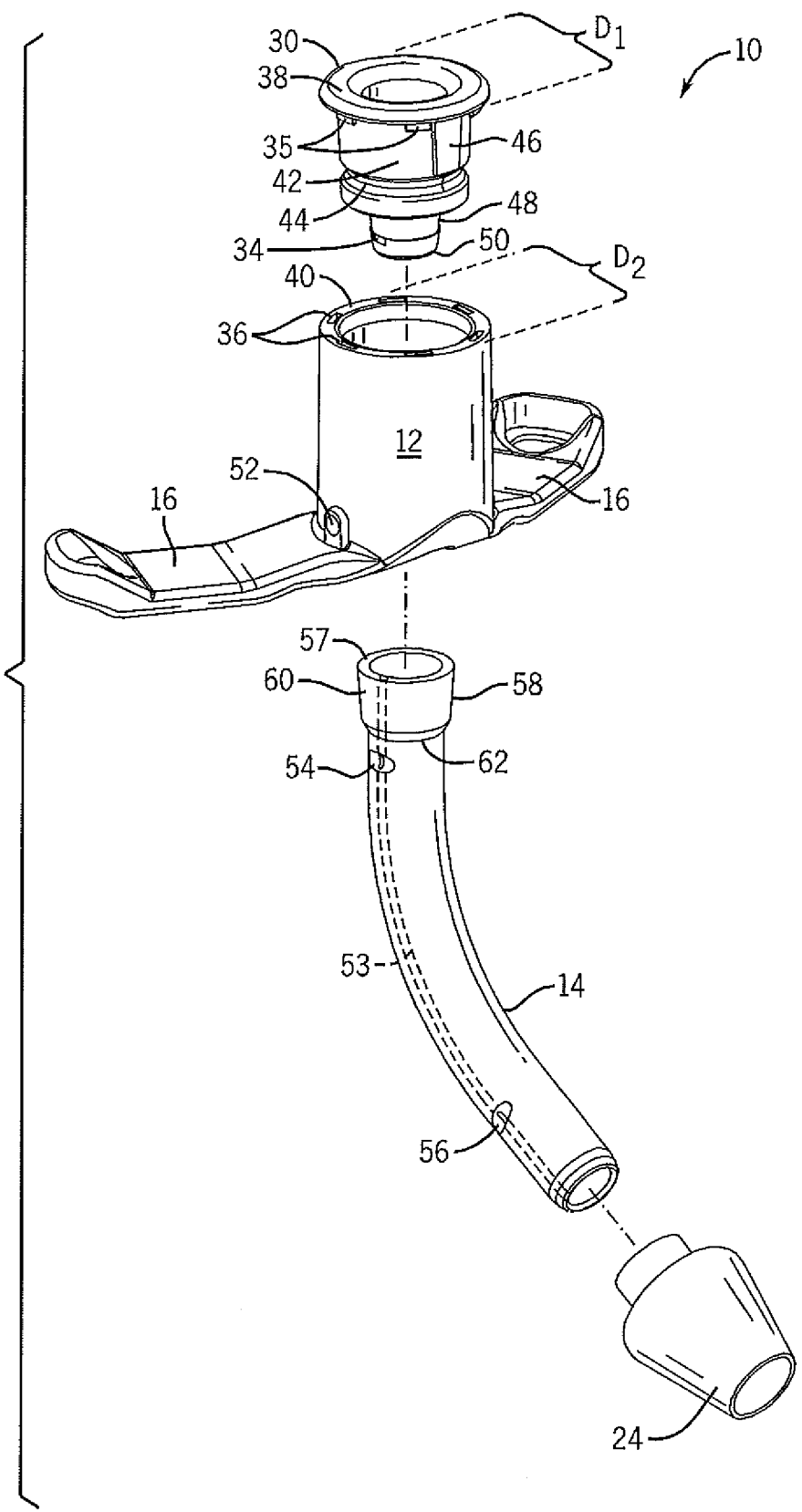
FIG. 2 is an exploded view of the same arrangement with an insert removed from the connector body.

FIG. 2 is an exploded view of embodiments of components of the tracheal tube 10, including at least one notch or recess 34 on the insert 30. The insert 30 also includes engageable teeth 35, capable of securing the insert 30 into the end connector 12. The engageable teeth 35 may be inserted into apertures or holes 36 of the end connector 12, and may aid in preventing the rotation of the insert 30 within the connector body. It is to be understood that while the depicted embodiment illustrates rectangular teeth, other embodiments may include pegs, triangular teeth, curved teeth, and so forth. Indeed, in another embodiment, the teeth 35 may be replaced with, for example, a full or sectional annular ridge. The annular ridge may then engage a conforming annular channel on the connector 12. In embodiments in which the insert 30 and the connector 12 are a unitary assembly, the assembly may not include engagable teeth 35 or holes 36, because the insert 30 is not separable from or capable of rotation relative to the connector 12.

Moreover, the insert 30 may include a proximal flange forming a surface 38 (i.e., "top" surface) that may substantially surround a proximal end 40 of the connector 12. This flange may have substantially the same radial dimension as the connector body. That is, in one embodiment, the top surface 38 may include an outer diameter $D_1$ slightly smaller to an outer diameter $D_2$ of the proximal end 40. For example, $D_1$ may be approximately between $\frac{1}{1,000}$ in. to $\frac{1}{50}$ in. smaller than $D_2$. The slight size difference between $D_1$ and $D_2$ prevents $D_1$ from creating an interference fit with a corresponding ventilator connector (e.g., female end connector) that may be coupled to the end connector 12. The end connector body may create an interference fit suitable for securing, for example, the female end connector to the connector 12. In another embodiment, the outer diameter $D_1$ may be approximately equal to the outer diameter $D_2$. By "covering" the proximal end 40, the top surface 38 may reduce or eliminate the number of interstices (e.g., spaces or gaps) included in the tracheal tube 10, thus reducing the locations that may harbor bacteria. The figure is also illustrative of how the various components of the tracheal tube 10 may be assembled or manufactured.

The insert 30 includes a body 42. In certain embodiments, the body 42 may be a generally tapered body 42. In other embodiments, the body 42 may be a generally cylindrical body 42. In the particular embodiment illustrated, a groove 44 is provided near the lower end of the insert, and this groove 44 will interface with a conforming feature of the connector body when inserted, as also described below. Moreover, a flat or other key structure 46 is provided that also aids in preventing rotation of the insert within the connector body. Also visible in FIG. 2 is a lower extremity 48 of the insert. As described with particular reference to FIG. 5, this lower extremity 48 is configured to conform to an upper end of the cannula 14. The lower extremity 48, in turn, has a tapered portion 50 that interfaces with the cannula as described below. In certain embodiments, the inner surface of the end connector body may be coated with a glue so as to securely couple the cannula 14 and/or insert 30 to the end connector body.

The connector 12 includes an aperture 52 suitable for enabling the insertion of the inflation lumen 28 (shown in FIG. 1). A fluid such as air may be delivered to the cuff 24, for example, through the inflation lumen 28, via an internal cannula lumen 53 having openings 54 and 56. The lumen 53 is formed in a cannula wall 57 defining a passageway through the cannula 14. Accordingly, the cuff 24 may be inflated to comfortably seal the patient's airway. The cannula itself has a proximal end 58 which forms a tapered upper section 60 configured to fit against the inner surface of the connector body as described below. A lower tapered section 62 also contacts and interfaces with the inner surface of the connector body to retain the cannula in place within the connector. The four components 12, 14, 24 and 30, will typically be formed separately. The connector 12 and insert 30 will typically be molded, while the cannula 14 may be made by an extrusion process. Other processes may, of course, be employed where desired and appropriate.

In a presently contemplated embodiment, the connector 12 is made of a soft polyvinylchloride or other plastic. The soft material of the connector allows for easy gripping and a good contact fit with the mating connector part when the tube is connected to a ventilation system. The softer material also allows for comfort against the patient's neck. The flanges 16 may also be molded with the body of the connector 12, or these could be added in a separate operation. In a presently contemplated embodiment, the flanges 16 are co-molded or over-molded with the connector body. The cannula 14 may also be made of a plastic material, such as soft polyvinylchloride, polyurethane, thermoplastic elastomers, or other plastics. The insert 30 may be made of a harder material than the connector body, such as a hard polyvinylchloride, a polycarbonate plastic, ABS, or any suitable material or a combination of materials. Where the insert is harder than the soft connector body, it provides rigidity to a connector body and resists forces that might tend to collapse the connector body, such as from mating connectors, and so forth. The more rigid structure also provides a good surface to which the cannula may be bonded, and that supports the inner diameter of the cannula.

In one embodiment, the assembly may be performed by first inserting the insert 30 into the cannula 14. The recess 34 is aligned with the lumen 53 at its proximal end 58 such that the lumen 53 is capable of expanding into the recess 34. To that end, the cannula 14 or the insert 30 may include addition alignment guides or indicators to facilitate the correct alignment. Upon insertion of the insert 30, the lower extremity 48 may be concentrically or co-axially inserted into the proximal end 58 by applying a mechanical force. Various fastening techniques may be used to secure the insert 30 to the cannula 14. In one example, a solvent bonding or solvent welding is used. In this example, a solvent is used to coat the mating surfaces of the insert 30 and cannula 14 to fasten the two components. An interference or compression fit and the evaporation and/or thermal activation of the solvent may result in a strong bonding of the insert 30 to the cannula 14. In this example, the solvent bonding may reduce undesirable adhesive or glue residue. In another example, an adhesive or glue may be used. The adhesive may be applied to the outer surface of the lower extremity 48 and/or the inner surface of the proximal end 58, thus securely fastening the two components to each other. For example, a cyanoacrylate glue may be used to fasten the two components 48 and 58 to each other.

Both the cannula 14 and the insert 30 may then be inserted into the connector 12, such that the cannula lower end extends through the connector 12 and the cannula seats within the connector as described below. During insertion, the teeth 35 are aligned with the apertures 36 and the insert 30 is aligned with the connector inner surface and pressed into place. In the present embodiment, the retention features of the insert 30, such as teeth 35 and groove 44, cooperating with those of the connector 12, prevent the insert from being easily removed from the connector. Although mechanical features are built into the connector and insert in the embodiment illustrated, such mechanical features may be complimented by various bonding agents and/or adhesives. For example, the solvent bonding or solvent welding technique described above may be used to securely bond the insert (and cannula 14), to the connector 12. In certain embodiments, the insert 30 and connector body may be co-molded or over-molded. In another embodiment, a fastening component may then be inserted through the bottom of the connector 12 and fastened in place. The cuff 24 may then be disposed in the distal end of the cannula 14, and aligned over the opening 56. Both the fastening component and the cuff 24 may then be secured through the use of various bonding agents and/or adhesives. It should be noted that the assembly may proceed in different orders (e.g., by insertion of the cannula 14 in the connector with or separately from the insert 30), depending upon the particular configuration of the components, the nature of the retaining features of each, and the type of processes used for formation and assembly (e.g., solvent bonding, overmolding, etc.).

Figure 3:
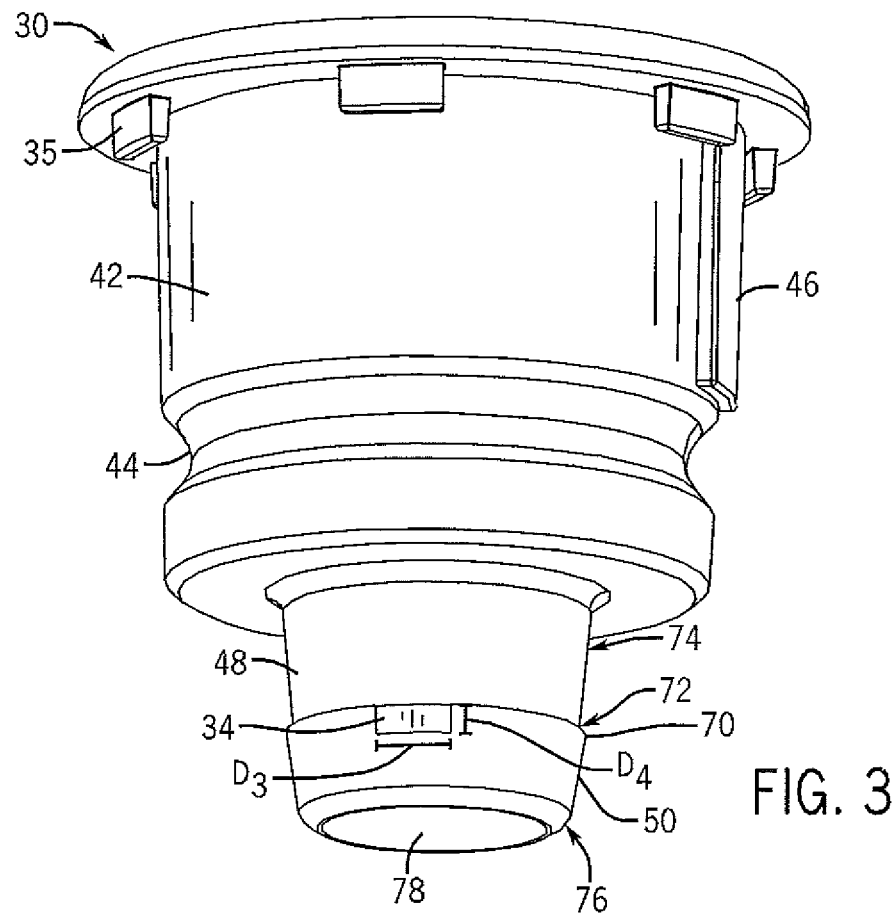
FIG. 3 is a perspective view of the connector insert of FIG. 1.

FIG. 3 is a perspective view of the insert 30 showing the recess 34. It should be understood that the insert 30 may include a plurality of recesses 34 configured to be aligned with a respective plurality of secondary lumens. The recess 34 is located on the inserted lower extremity 48 at a step 70 formed at the junction 72 of a first region, e.g., the tapered portion 50, and a second region, e.g., a more proximal portion 74 of the lower extremity. The step 70 is an increase in diameter of the tapered portion 50 relative to the adjacent diameter of the proximal portion 74 at the junction 72. In particular embodiments, the proximal portion 74 may have a substantially constant diameter or may taper towards a distal end 76. The widest diameter at the step 70 may be approximately the same as the inner diameter of the cannula 14 or, in certain embodiments, may be slightly smaller than the inner diameter of the cannula 14. The insert 30 defines a passageway 78. The taper of the tapered portion 50 may translate to a corresponding tapering inner diameter of the passageway 78. Alternatively, the inner diameter of the passageway 78 in the area corresponding to the tapered portion 50 may be substantially constant.

The recess 34 may be any suitable size or shape. In particular, depending on the size and depth of the recess 34, the amount of stress on the lumen 53 may be controlled. In certain embodiments, the recess 34 may be at least as wide as the lumen 34. The width $D_3$ represents a portion of the circumference of the step 70 occupied by the recess 34. In a particular embodiment, the recess 34 may encompass an arc of 30 degrees or less of the circumference around the step 70. In addition, the recess 34 may be characterized by its height $D_4$ along the insert 30. In one embodiment, $D_3$ is larger than $D_4$ such that the recess 34 is generally rectangular. In another embodiment, the width $D_3$ and height $D_4$ may be at least 0.1 mm to about 3 mm. The recess 34 may be aligned with respect to other features on the insert 34. For example, the recess 34 may be aligned with an engageable tooth feature 35. In addition, the recesses 34 may be aligned and/or offset from the key 46. In a particular embodiment, the recess 34 may be aligned with the key 46 to facilitate alignment of the recess 34 with the lumen 53. In particular, the key 46 is larger than the recess 34 and easier to visualize during the insertion of the insert 30 in the cannula 14.

Figure 4:
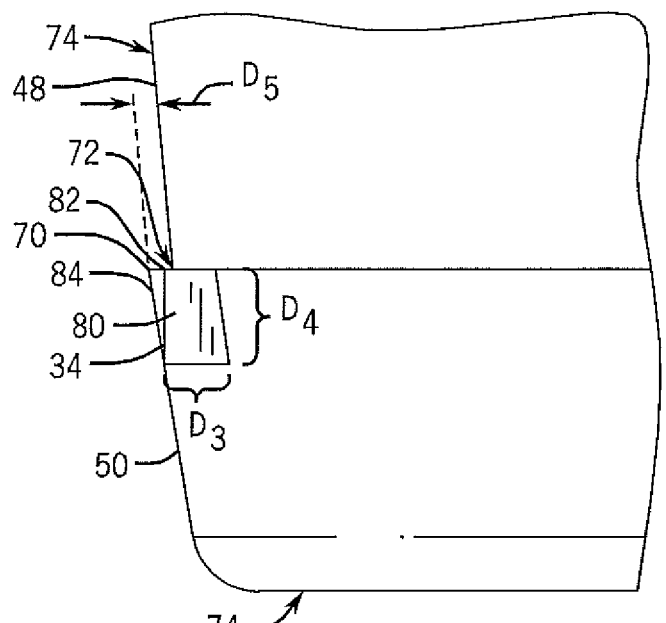
FIG. 4 is a detail view of the stepped region of the connector insert of FIG. 1.

FIG. 4 is a detail view of the tapered portion 50 and recess 34 of the insert 30 showing an addition dimension, $D_5$, representing a depth of the recess relative to the step 70. The depth $D_5$ may be at least 0.1 mm or 0.15 mm and, in certain embodiments, may be about 0.1 mm to about 0.5 mm. Further, the depth $D_5$ may be selected based on the size of the cannula 14 and its corresponding insert 30. The recess 34 may have a sloped or tapered surface 80. That is, the depth $D_5$ of the recess 34 may change over the height $D_4$. In this manner, the recess 34 allows greater expansion of the cannula 14 at an area corresponding to the greatest applied stress, i.e., at step 70, while the recess is smaller at areas of the tapered portion 50 that apply less stress (e.g., because they have a relatively smaller outer diameter than the step 70). In certain embodiments, the depth $D_5$ of the recess is such that the proximal end 82 is about flush with the proximal portion 74 at the junction 72. In other embodiments, the proximal end 82 protrudes slightly from the junction 72. The recess 34 is surrounded by wings 84 in the tapered portion that seal the insert 30 around the recess 34.

Figure 5:
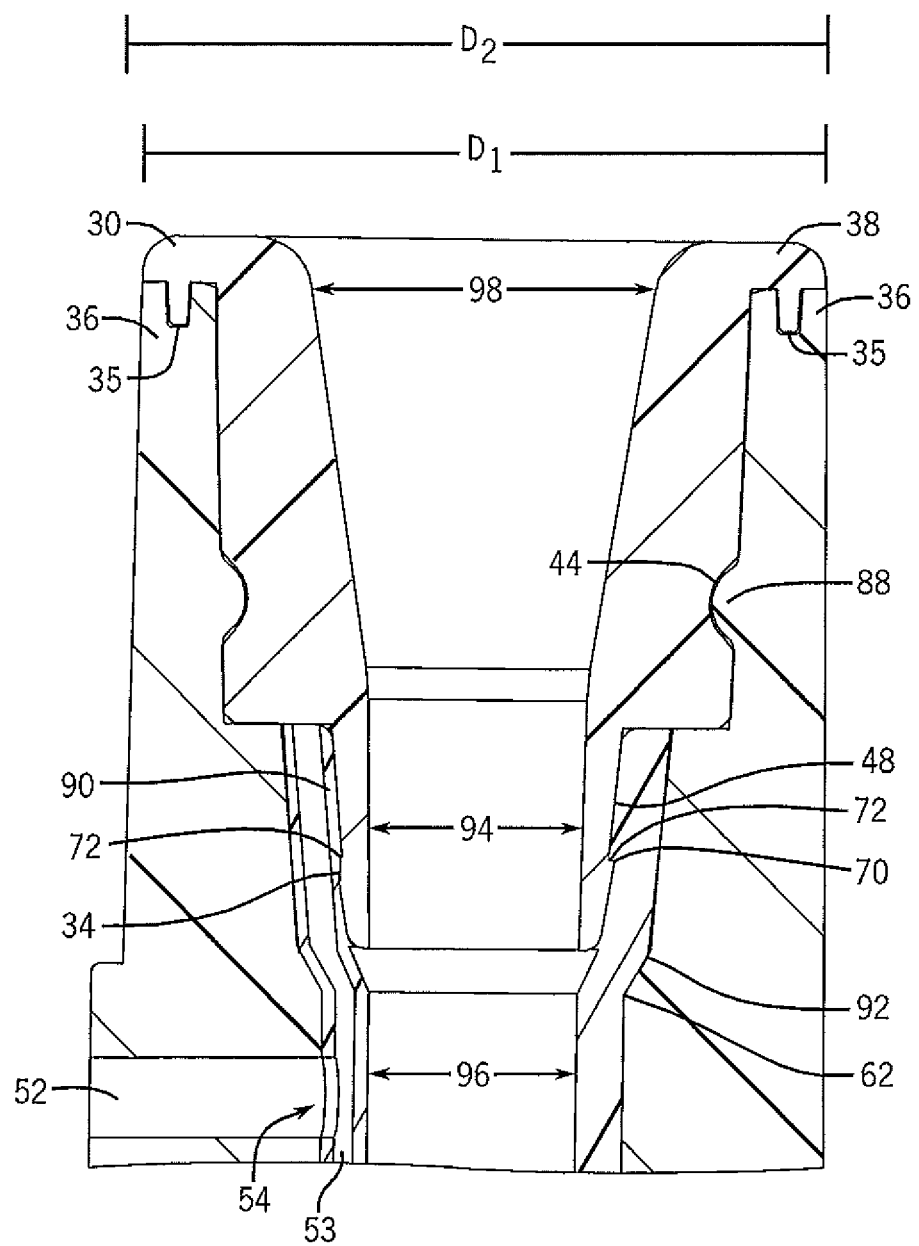
FIG. 5 is a sectional view of the tracheal tube of FIG. 1, illustrating internal features of the connector body, the insert, and the cannula when the three are joined in the completed tracheal tube.

FIG. 5 illustrates the three components 12, 14, and 30 of the tracheal tube in section. As described above, when assembled, the cannula 14 is lodged within the connector body, and retained in place by the insert 30. Moreover, the flat structure 46 illustrated in FIG. 2 cooperates with a similar surface of the connector body to prevent rotation of the insert within the connector body. The flat structure 46 may also be used as an assembly aid to facilitate alignment of the insert 30 with respect to the end connector 12 body. Further, the flat structure 46 may be used as a "keying" feature for repeatable positioning on a semi-automated assembly fixture.

In the arrangement shown in FIG. 5, moreover, an inner protrusion 88 of the connector body enters into groove 44 of the insert 30 to mechanically retain the insert 30 within the connector body. Likewise, the teeth 35 enter the apertures 36 of the insert 30 to aid in securing the insert 30 to the connector 12 and in maintaining the alignment of the insert 30 co-axially with respect to the connector 12. Here again, adhesives and bonding agents may also be employed to retain these components in the assembled positions shown in FIG. 5. Still further, the lower tapered section 50 of the insert 30 (see FIG. 2) is configured to conform to an inner wall section 90 of the cannula 14. The lower tapered section 62 of the cannula upper end (see FIG. 2) similarly conforms generally to a lower tapered inner wall section 92 of the connector body. Thus, the insert 30, which fits within the upper end of the cannula 14, tends to expand or compress the upper end of the cannula 14 slightly against the inner surface of the connector body. The recess 34 facilitates redirection of the compression forces away from the lumen 53. This cooperation retains the cannula 14 within the connector body, and prevents rotation of the cannula 14 with the connector body while preventing splitting of the cannula around the lumen 53.

It should be noted that the sizes of these components may be adapted to conform to various standard sizes of tracheal tubes. For example, in tubes used for pediatric and neonatal patients, an inner diameter of the cannula may vary between 2.5 and 6.5 mm. Other sizes, could, of course, be accommodated. It should also be noted that as shown in FIG. 5, the outer diameter $D_1$ of the top surface 38 may be slightly smaller than the outer diameter $D_2$ of the connector body. Additionally, the inner diameter of the lower extremity of the insert 30, indicated by reference numeral 94, will generally conform to the inner diameter 96 of the cannula. This arrangement allows for the easy passage of air or other ventilation gasses without creating an obstruction either in the connector or the cannula. The upper end of the opening in the insert, indicated by reference numeral 98, preferably expands to allow for the channeling of air or ventilation gasses easily into the assembly. It should also be noted that a range of sizes of inserts may be accommodated for the same external dimension of the connector body. Thus, various sizes of inserts 30 may be designed to interface with various sizes of cannulas. This may be done while maintaining the configuration and even the size of the connector body the same. Thus, the same connector body may be used with different inserts and cannula sizes to obtain a family of tracheal tubes. It is to be understood that, in other embodiments, the end connector body may be modified to accommodate cannulas of different sizes.

Figure 6:
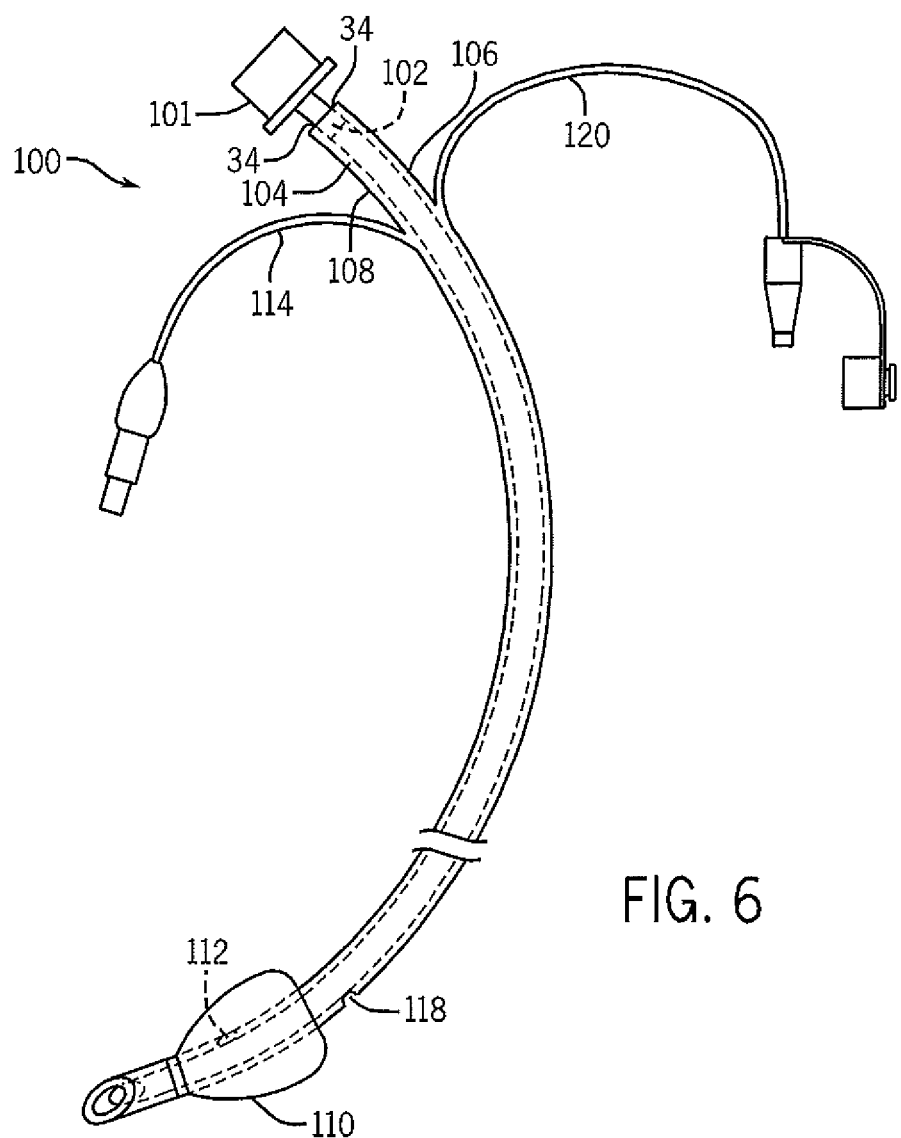
FIG. 6 is a partial perspective view of a connector as provided used in conjunction with an endotracheal tube.

FIG. 6 is a perspective view of an exemplary tracheal tube 100 including a connector end 101. As provided, the connector end 101 includes an inserted end 102 with a plurality of recesses 34 aligned with corresponding secondary lumens, i.e., cuff inflation lumen 104 and suction lumen 106, formed proximate to or within an exterior wall 108 of the tracheal tube 12. As shown, the tube 100 includes cuff 110 that may be inflated via the cuff inflation lumen 104. The lumen 104 opens via a notch 112 through the exterior wall 108 into the interior space of the cuff 110. The inflation lumen 104 is operatively connected to proximal inflation line 114, which may connect to a syringe or other inflation source. The tracheal tube 12 may also include suction lumen 106 for aspirating secretions that may form above the cuff 110 through opening 118. The suction lumen 106 connects to a proximal suction line 120 for connection to a suction source.

The tube 100 and the cuff 110 may be formed from materials having desirable mechanical properties (e.g., puncture resistance, pin hole resistance, tensile strength, and so forth) and desirable chemical properties (e.g., biocompatibility). Further, in one embodiment, the walls of the cuff 110 may be made of a polyurethane (e.g., Dow Pellethane® 2363-80A) having suitable mechanical and chemical properties. In other embodiments, the walls of the cuff 110 may be made of silicone or a suitable polyvinyl chloride (PVC). In certain embodiments, the cuff 110 may be generally sized and shaped as a high volume, low pressure cuff that may be designed to be inflated to pressures between about 15 cm $H_2O$ and 30 cm $H_2O$. Further, the cuff 110 may be a generally barrel-shaped cuff or a tapered cuff. In addition, to assist in proper placement of the tube 100, x-ray visible markings may be placed at any appropriate location. In certain embodiments, the tube 100 may be extruded. Secondary lumens, such the cuff inflation lumen 104 suction lumen 106, may be formed along or in the exterior wall of the tube 108 during the extrusion process. The connector end 101 may be generally more rigid that the extruded. It is envisioned that, in certain embodiments, the connector end 101 may be molded. Further, the connector end 101 may be inserted into and affixed to the tube 100 during the manufacturing process.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube comprising:
    a ventilation lumen having a proximal end and a distal end;
    a secondary lumen formed within a wall of the ventilation lumen; and
    a connector having a generally annular body and an insert portion defining a passageway that is in fluid communication with the ventilation lumen, wherein the insert portion is non-removably disposed within the annular body in the proximal end of the ventilation lumen such that the proximal end of the ventilation lumen is between the insert portion and the annular body, and wherein the insert portion comprises a first recess aligned with the secondary lumen and configured to reduce stress on the wall at least in the vicinity of the secondary lumen, wherein the first recess is disposed about only a portion of a circumference of a side wall of the insert portion at a step that is proximal to an insert distal end, wherein the step is formed at a junction of a tapered portion with a non-tapered portion.

2. The tracheal tube of claim 1, wherein the tapered portion is disposed on the insert distal end.

3. The tracheal tube of claim 2, wherein a widest diameter of the tapered portion is larger than an outer diameter of the non-tapered portion such that the tapered portion forms the step.

4. The tracheal tube of claim 3, wherein the first recess is disposed on a widest diameter portion of the tapered portion proximate the step.

5. The tracheal tube of claim 1, wherein the tracheal tube comprises an endotracheal tube.

6. The tracheal tube of claim 1, wherein the tracheal tube comprises a tracheostomy tube.

7. The tracheal tube of claim 1, wherein the connector comprises a pair of laterally extending flanges for facilitating securement to a patient.

8. The tracheal tube of claim 1, wherein an exterior portion of the connector that is outside of the ventilation lumen has an outer diameter of 15 mm.

9. The tracheal tube of claim 1, wherein the connector comprises a passageway configured to accommodate an inflation line for an inflatable balloon cuff, wherein the inflation line is in fluid communication with the secondary lumen.

10. The tracheal tube of claim 1, wherein the connector comprises a second recess circumferentially offset from the first recess, and wherein the second recess is aligned with an additional secondary lumen formed in or on the wall of the ventilation lumen.

11. The tracheal tube of claim 1, wherein the first recess comprises a width that is larger than a height of the first recess.

12. The tracheal tube of claim 11, wherein the width is at least as wide as the secondary lumen.

13. The tracheal tube of claim 11, wherein the first recess comprises a variable depth over the height such that the recess has a sloped surface.

14. A tracheal tube comprising:
a connector having a generally annular body;
a cannula having a proximal end disposed in the annular body; and
an insert disposed in the annular body and having a tubular lower extremity contacting the proximal end of the cannula to compress the cannula between the insert and an inner surface of the annular body to retain the cannula lodged within the annular body, wherein the insert comprises a notch encompassing an arc of 30 degrees or less on a side wall of the insert and at a step formed on the tubular lower extremity proximal to an insert distal end, and wherein a circumferential portion of the cannula in contact with the insert comprises a first portion in the vicinity of the notch that is less compressed relative to a second portion that is not in the vicinity of the notch.

15. The tracheal tube of claim 14, wherein the first portion in the vicinity of the notch comprises a lumen formed in a wall of the cannula.

16. The tracheal tube of claim 14, wherein the lower extremity comprises a tapered region and wherein the notch is disposed on a widest diameter of the taper.

17. The tracheal tube of claim 16, wherein the tapered region tapers towards the distal end of the insert.

18. The tracheal tube of claim 14, wherein the tubular lower extremity of the insert has a portion having an inner diameter approximately equal to an inner diameter of the cannula.

19. The tracheal tube of claim 14, wherein the annular body comprises an anti-rotation feature that interfaces with the insert to prevent rotation of the insert within the annular body.

20. The tracheal tube of claim 19, wherein the insert comprises a plurality of circumferentially spaced barbs configured to mate with the anti-rotation feature of the annular body.

* * * * *